US012774440B2

(12) United States Patent
Jang et al.

(10) Patent No.: US 12,774,440 B2
(45) **Date of Patent: *Oct. 27, 2026**

(54) CELL CULTURE APPARATUS

(71) Applicant: AMOGREENTECH CO., LTD., Gimpo-si (KR)

(72) Inventors: Seon Ho Jang, Gyeonggi-do (KR); Kyoung Ku Han, Gyeonggi-do (KR)

(73) Assignee: AMOGREENTECH CO., LTD., Gimpo-si (KR)

( * ) Notice: Subject to any disclaimer, the term of this patent is extended or adjusted under 35 U.S.C. 154(b) by 1035 days.

This patent is subject to a terminal disclaimer.

(21) Appl. No.: 17/780,684

(22) PCT Filed: Nov. 9, 2020

(86) PCT No.: PCT/KR2020/015619
§ 371 (c)(1),
(2) Date: May 27, 2022

(87) PCT Pub. No.: WO2021/107450
PCT Pub. Date: Jun. 3, 2021

(65) Prior Publication Data

US 2023/0357692 A1 Nov. 9, 2023

(30) Foreign Application Priority Data

Nov. 29, 2019 (KR) ........................ 10-2019-0157324

(51) Int. Cl.
*C12M 1/12* (2006.01)
*C12M 1/00* (2006.01)
*C12M 3/00* (2006.01)

(52) U.S. Cl.
CPC ............ *C12M 25/02* (2013.01); *C12M 23/40* (2013.01); *C12M 23/42* (2013.01); *C12M 29/16* (2013.01)

(58) Field of Classification Search
CPC ...... C12M 25/02; C12M 23/40; C12M 23/42; C12M 29/16
See application file for complete search history.

(56) References Cited

U.S. PATENT DOCUMENTS 4,311,593 A 1/1982 Benjes et al.
4,661,455 A 4/1987 Hubbard
(Continued)

FOREIGN PATENT DOCUMENTS

CN 112980689 A 6/2021
CN 113015785 A 6/2021
(Continued)

OTHER PUBLICATIONS

Chinese Office Action for Chinese Application No. 202080082777.0. dated Jan. 11, 2025 (10 pages).
(Continued)

*Primary Examiner* — William H. Beisner
*Assistant Examiner* — Danielle B Henkel
(74) *Attorney, Agent, or Firm* — ROTHWELL, FIGG, ERNST & MANBECK, P.C.

(57) ABSTRACT

A cell culture apparatus is provided. A cell culture apparatus according to an exemplary embodiment of the present invention comprises: a housing having an internal space which is filled with a culture medium for cell culture; and a support assembly which is provided in a plate form having a predetermined area, comprises a plurality of supports provided in multiple stages at a certain distance apart from each other in one direction, and is inserted in the internal space in the state where the plurality of supports are coupled to each other via at least one fastening bar.

11 Claims, 15 Drawing Sheets

(56) References Cited

U.S. PATENT DOCUMENTS

| | | | | |
|---|---|---|---|---|
| 5,260,211 | A | 11/1993 | Matsuda et al. | |
| 5,369,494 | A | 11/1994 | Bowden | |
| 5,605,835 | A * | 2/1997 | Hu | C12M 25/12 435/297.2 |
| 8,518,692 | B2 | 8/2013 | Wilson | |
| 9,226,494 | B2 | 1/2016 | Chang | |
| 9,255,243 | B2 * | 2/2016 | Wilson | C12N 5/0602 |
| 9,290,730 | B2 | 3/2016 | Martin | |
| 9,441,192 | B2 | 9/2016 | Wilson et al. | |
| 10,889,792 | B2 * | 1/2021 | Griffin | C12M 25/06 |
| 2003/0017142 | A1 * | 1/2003 | Toner | A61M 1/3472 435/370 |
| 2003/0157709 | A1 | 8/2003 | Dimilla | |
| 2004/0072347 | A1 * | 4/2004 | Schuler | C12M 23/08 435/372 |
| 2010/0055774 | A1 * | 3/2010 | Wilson | C12M 23/40 435/289.1 |
| 2010/0304472 | A1 * | 12/2010 | Kim | C12M 23/44 435/304.1 |
| 2011/0212493 | A1 | 9/2011 | Hirschel et al. | |
| 2013/0059339 | A1 * | 3/2013 | Karerangabo | C12M 41/46 435/235.1 |
| 2015/0056703 | A1 * | 2/2015 | Johnson | C12N 5/0667 435/289.1 |
| 2016/0083685 | A1 * | 3/2016 | Niazi | C12M 25/16 435/308.1 |
| 2018/0057784 | A1 | 3/2018 | Wang | |
| 2018/0201891 | A1 * | 7/2018 | Ubukata | C12M 23/22 |
| 2020/0318049 | A1 | 10/2020 | Koo et al. | |
| 2022/0002654 | A1 | 1/2022 | Jang et al. | |
| 2024/0409865 | A1 * | 12/2024 | Jang | C12M 1/12 |

FOREIGN PATENT DOCUMENTS

| | | | |
|---|---|---|---|
| JP | 2012-506257 | A | 3/2012 |
| JP | 2016-174614 | A | 10/2016 |
| JP | 2017085960 | A | 5/2017 |
| JP | 2018023291 | A | 2/2018 |
| JP | 2021-522826 | A | 9/2021 |
| KR | 10-2010-0088297 | A | 8/2010 |
| KR | 10-2016-0001349 | A | 1/2016 |
| KR | 10-2017-0008024 | A | 1/2017 |
| KR | 10-2017-0135769 | A | 12/2017 |
| KR | 10-1910118 | B1 | 10/2018 |
| KR | 10-2019-0039584 | A | 4/2019 |
| KR | 10-2021-0046117 | A | 4/2021 |
| KR | 20210067562 | A | 6/2021 |
| WO | 2021/075806 | A1 | 4/2021 |

OTHER PUBLICATIONS

International Search Report in PCT/KR2020/015619 dated Feb. 26, 2021, 4 pages.

Non-Final Office Action for related U.S. Appl. No. 17/293,741 dated Jan. 28, 2026 (16 pages).

Extended European Search Report for EP Application No. 22878746.1 dated Jun. 19, 2026. (8 pages).

Final Office Action in related U.S. Appl. No. 17/293,741 dated Jul. 29, 2026 (19 pages).

ThermoFisher Scientific; "Amine-Reactive Crosslinker Chemistry", Protein Biology Resource Library; <https://web.archive.org/web/20190922145511/https://www.thermofisher.com/us/en/home/life-science/protein-biology/protein-biology-leaming-center/protein-biology-resource-library/pierce-protein-methods/amine-reactive-crosslinker-chemistry.html>; 8 pages (2019).

Non-Final Office Action for corresponding U.S. Appl. No. 17/788,868 dated Aug. 25, 2026. (11 pages).

* cited by examiner

CELL CULTURE APPARATUS

CROSS-REFERENCE TO RELATED APPLICATIONS

This application is the national phase entry of International Application No. PCT/KR2020/015619, filed on Nov. 9, 2020, which is based upon and claims priority to Korean Patent Applications 10-2019-0157324, filed on Nov. 29, 2019, the entire contents of which are incorporated herein by reference.

TECHNICAL FIELD

The present invention relates to a cell culture apparatus, and more particularly, to a cell culture apparatus capable of culturing a large number of cells at one time.

BACKGROUND

Cell culture is a method of culturing or proliferating cells by removing a piece of tissue from a multicellular organism and then supplying nutrients to the removed piece of tissue in a container.

In the field of biotechnology, which has been rapidly developing since the 1980s, animal cell culture technology plays an important role in relation to the industrialization of biological drugs. Accordingly, from the mid-1980s, the importance of animal cell mass culture technology began to be emphasized.

The animal cells derived from human or animal tissues can be cultured while suspended in a culture medium or attached to a carrier. The cells derived from blood cells (including hematopoietic stem cells) are mainly suspension cells, and the cells derived from tissues such as skin, liver or lungs, embryonic stem cells or mesenchymal stem cells are adherent cells. Suspension cells can proliferate when suspended in the culture medium alone, but adherent cells can only proliferate when attached to the surface of a support.

Accordingly, in order to maintain the highest cell density per unit volume during cell scale-up, suspension cells are advantageous, so the cell mass culture method has mainly been made only for suspension cells, but the development of methods or apparatus for mass culture of adherent cells is insufficient.

SUMMARY OF THE INVENTION

The present invention has been devised in view of the above points, and an object of the present invention is to provide a cell culture apparatus capable of being used in a cell culture system for culturing adherent cells in large quantities through one process.

Another object of the present invention is to provide a cell culture apparatus capable of increasing mass productivity.

Moreover, another object of the present invention is to provide a cell culture apparatus to which a support having a large area can be applied.

In order to achieve the above object, the present invention provides a cell culture apparatus, including a housing including an internal space filled with a culture medium for cell culture; and a support assembly provided in a plate shape having a predetermined area, and including a plurality of supports disposed in multiple stages in a state spaced apart from each other at a predetermined interval along one direction, wherein the support assembly is inserted in the internal space in a state where the plurality of supports is coupled to each other via at least one fastening bar.

In addition, the housing may include a first box-shaped housing having a first internal space with an open lower portion, and a second box-shaped housing detachably coupled to the first housing and having a second internal space with an open upper portion, and the internal space may be formed by connecting the first internal space and the second internal space to each other when the first and second housings are combined.

In this case, the first housing and the second housing may be formed to have different heights, and an inlet for supplying the culture medium to the internal space may be formed in the housing having a larger height among the first housing and the second housing.

In addition, the housing may include an inlet for supplying the culture medium to the internal space, and an internal surface of the housing in which the inlet is formed may be formed of a plurality of stepped surfaces whose cross-sectional area increases from the inlet toward an edge.

In addition, the support may be formed in a polygonal shape having a straight side and a pair of inclined sides extending in a direction away from each other while being inclined at a predetermined angle from both ends of the straight side, and an inlet for supplying the culture medium to the internal space may be formed in the housing to be positioned at a position corresponding to the straight side.

In this case, the housing may include a first box-shaped housing having a first internal space with an open lower portion, and a second box-shaped housing detachably coupled to the first housing and having a second internal space with an open upper portion, the second housing may be formed to have a height different from that of the first housing, and the inlet for supplying the culture medium to the internal space may be formed in the housing having a larger height among the first housing and the second housing. Alternatively, the housing may include a box-shaped body having the internal space with an open upper portion, and a cover fastened to the body to cover the open upper portion of the internal space.

In addition, the support may include a plate-shaped nanofiber membrane coated with a protein motif, and a support member attached to one surface of the nanofiber membrane via an adhesive layer to support the nanofiber membrane.

In addition, the support may be a plasma-treated plate-shaped film member.

As an example, the support assembly may include a pair of support plates provided in a plate shape having a predetermined area, the plurality of supports disposed in multiple stages between the pair of support plates, a spacer disposed between the plurality of supports to space the two supports apart from each other, a plurality of the fastening bars for mutually fastening the pair of support plates, the plurality of supports, and the spacer, and a fastening member fastened to both ends of the fastening bar so that the pair of support plates and the plurality of supports are able to maintain a state fastened to the fastening bar, the support plate may include a receiving groove formed to be drawn inward from one surface to a predetermined depth, and the fastening member may be accommodated in the receiving groove and may be prevented from protruding outward.

As another example, the support assembly may include a pair of support plates provided in a plate shape having a predetermined area, the plurality of supports disposed in multiple stages between the pair of support plates, a spacer disposed between the plurality of supports to space the two supports apart from each other, and a plurality of the fastening bars for mutually fastening the pair of support plates, the plurality of supports, and the spacer, the fastening bar may include protruding portions each protruding to an outside of the pair of support plates, and the protruding portions may be melted through thermal fusion and fixed to one surface of the support plate.

In addition, the spacer may include a pair of first spacers having a predetermined length and formed in a plate shape, and the pair of first spacers may be disposed to be positioned at both ends along a width direction of the support.

In this case, the spacer may further include at least one second spacer formed in a ring shape, and the second spacer may be disposed to be positioned in an internal region of the support.

According to the present invention, a large number of cells can be cultured at one time, so that productivity can be improved, costs can be reduced, and uniformity of quality can be maintained.

In addition, according to the present invention, a plurality of supports is configured in an assembly form integrated with each other, and a first housing and a second housing are coupled to each other to form a single housing, thereby increasing mass productivity.

In addition, according to the present invention, even if a support is composed of a large area, it is possible to increase a culture area by reducing a dead space and to be in contact with a culture medium smoothly, so that a larger amount of cells can be cultured in large quantities.

DETAILED DESCRIPTION

Figure 1:
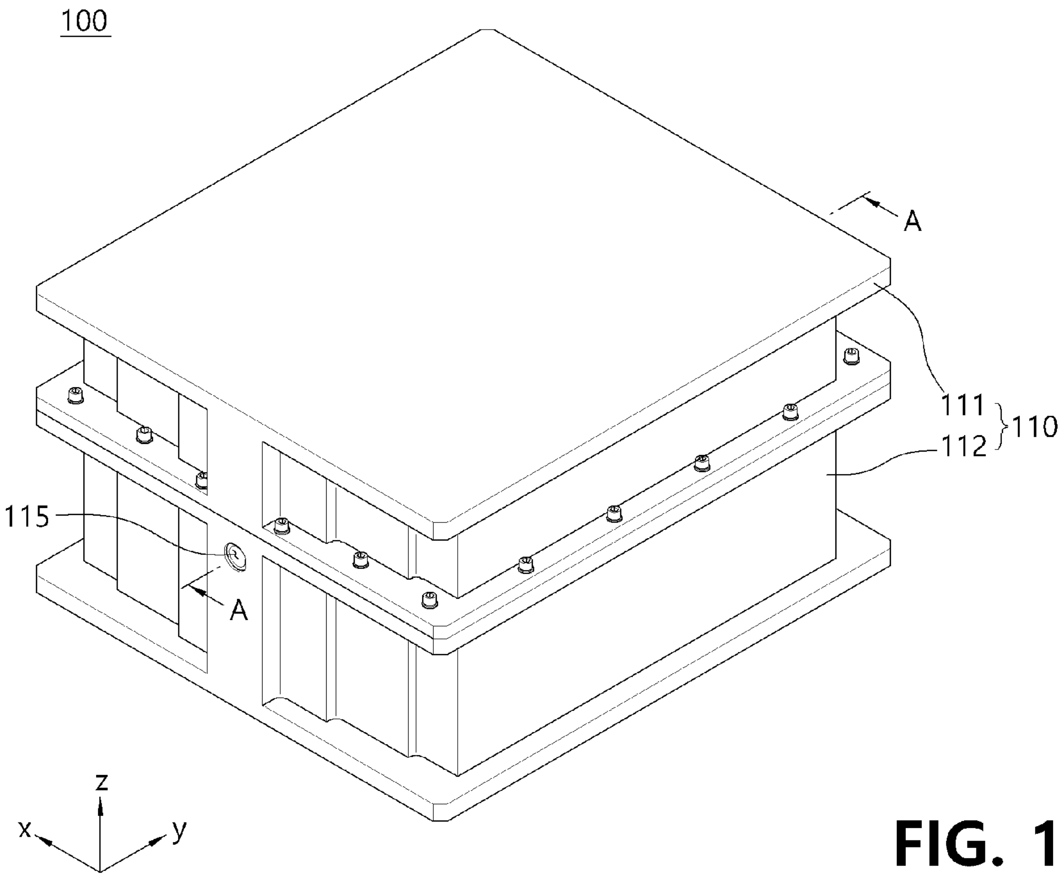
FIG. 1 is a view showing a cell culture apparatus according to an embodiment of the present invention.

Hereinafter, with reference to the accompanying drawings, embodiments of the present invention will be described in detail so that those of ordinary skill in the art to which the present invention pertains can easily implement them. The present invention may be embodied in many different forms and is not limited to the embodiments described herein. In order to clearly explain the present invention in the drawings, parts irrelevant to the description are omitted, and the same reference numerals are added to the same or similar components throughout the specification.

The cell culture apparatus 100, 200, 300 according to an embodiment of the present invention includes a housing 110, 210, 310 and a support assembly 120, 220, 320 as shown in FIGS. 1 to 12.

Figure 5:
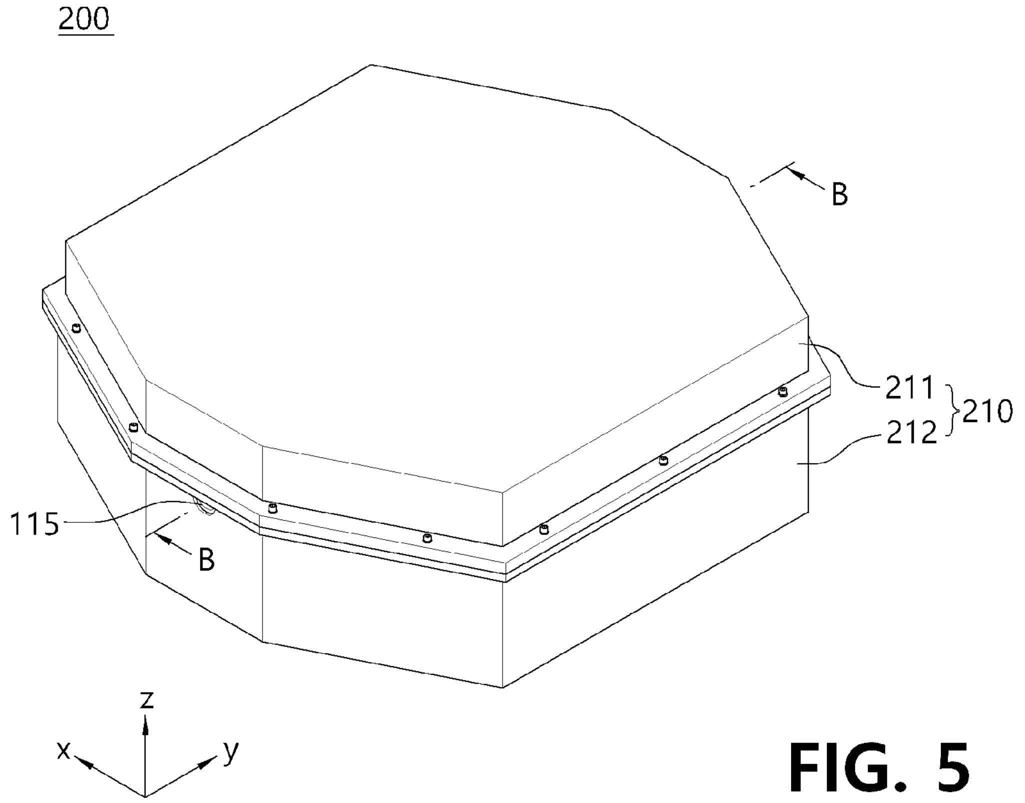
FIG. 5 is a view showing a cell culture apparatus according to another embodiment of the present invention.
Figure 9:
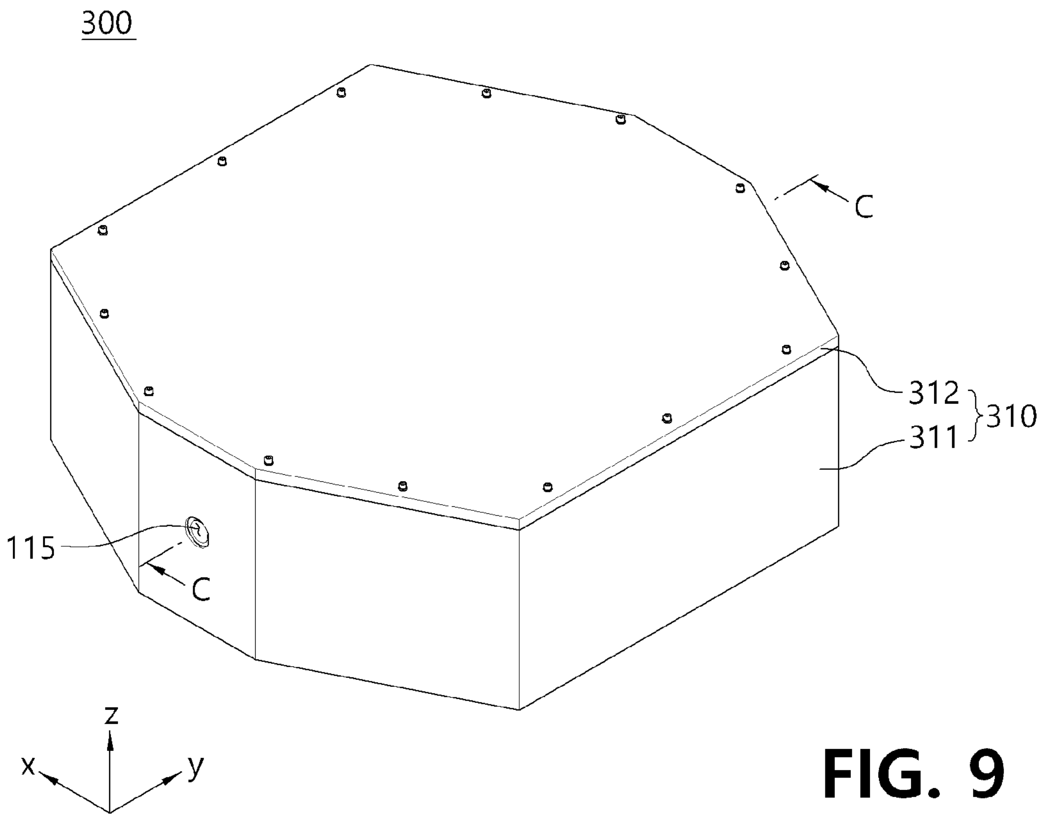
FIG. 9 is a view showing a cell culture apparatus according to still another embodiment of the present invention.
Figure 10:
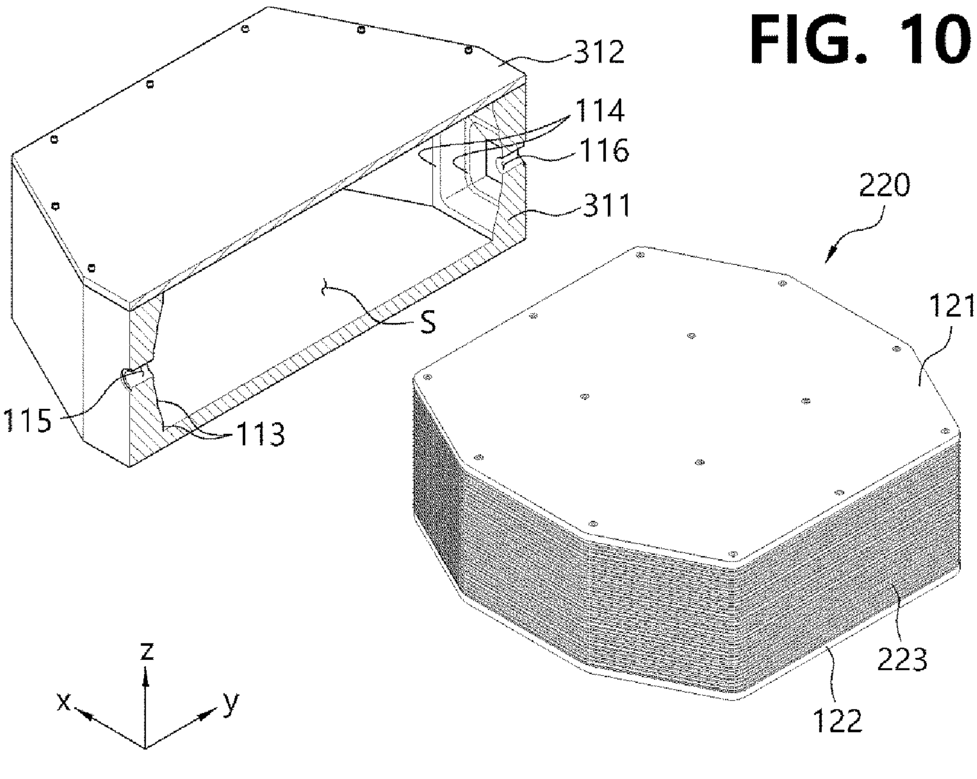
FIG. 10 is a view showing a state in which a support assembly is exploded after cutting a portion of the housing in FIG. 9.
Figure 11:
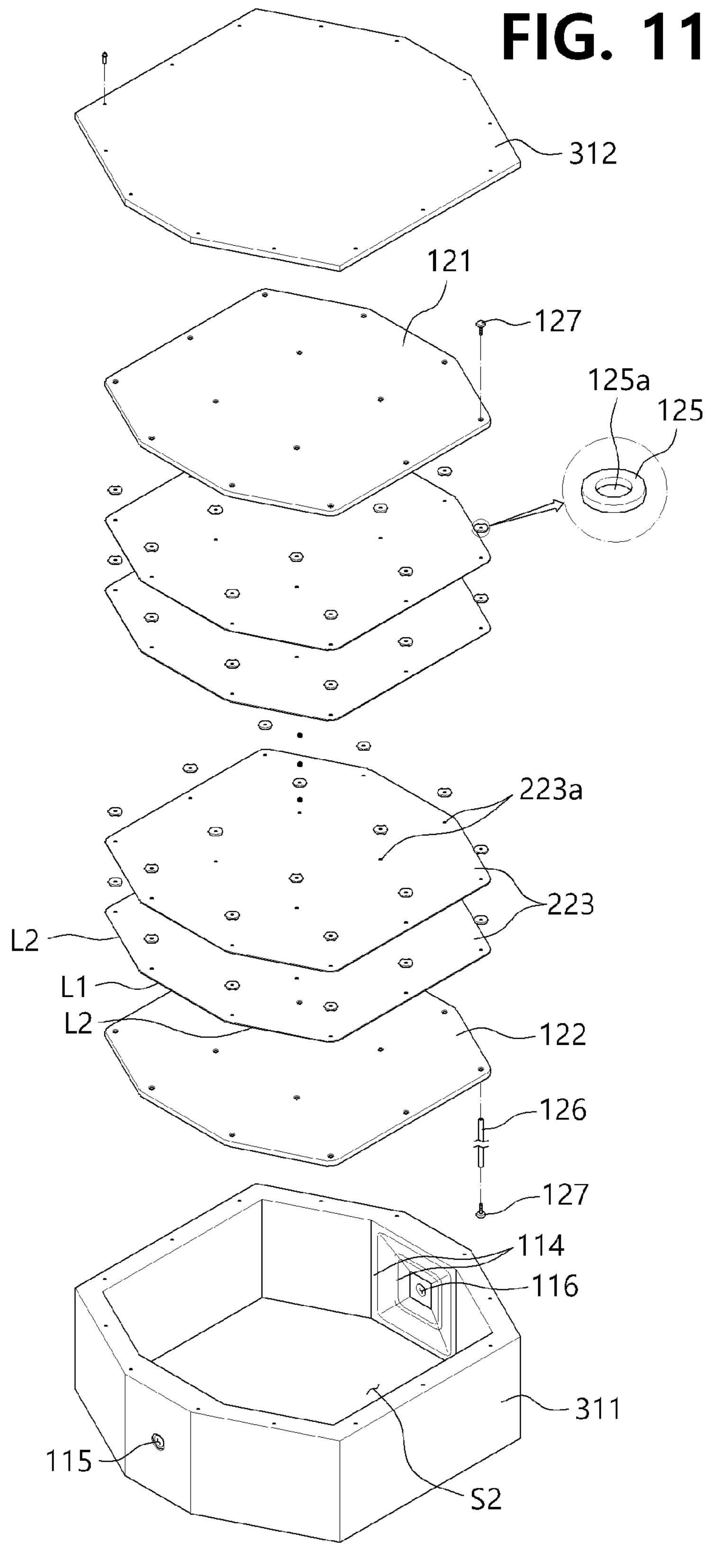
FIG. 11 is an exploded view of FIG. 9.

In this specification, a width direction, left and right directions, and a side surface may be defined in a direction parallel to the X-axis in FIGS. 1, 5 and 9, a longitudinal direction, front and rear directions, front and rear sides may be defined in a direction parallel to the Y axis in FIGS. 1, 5 and 9, and a height direction, up and down directions, upper and lower surfaces may be defined in a direction parallel to the Z axis in FIGS. 1, 5 and 9.

The housing 110, 210, 310 can accommodate the support assembly 120, 220, 320 for cell culture therein. Through this. the housing 110, 210, 310 may provide a culture space for culturing cells attached to a plurality of supports 123, 223 constituting the support assembly 120, 220, 320.

For this, the housing 110, 210, 310 may be formed in a box shape having an internal space (S), and an inlet 115 and an outlet 116 may be formed at one side of the housing 110, 210, 310, respectively.

Accordingly, the culture medium supplied from an outside may be supplied to the internal space (S) side through the inlet 115, and the culture medium accommodated in the internal space (S) may be discharged to the outside through the outlet 116.

Through this, the culture medium supplied to the housing 110, 210, 310 from the outside can fill the internal space (S) through the inlet 115, and after the cell culture is completed, the culture medium filled in the internal space (S) may be discharged to the outside through the outlet 116.

Accordingly, the support assembly 120, 220, 320 disposed in the internal space (S) may be submerged in the culture medium filling the internal space (S), and the cells attached to the respective supports 123, 223 constituting the support assembly 120, 220, 320 may smoothly receive nutrients required for cell culture from the culture medium.

In this case, the internal surface of the housing in which the inlet 115 is formed may include a plurality of stepped surfaces 113 formed in a form in which the cross-sectional area increases from the inlet 115 toward an edge.

That is, the internal surface of the housing 110, 210, 310 in which the inlet 115 is formed has a plurality of stepped surfaces 113 formed in a form in which the cross-sectional area increases along the direction in which the culture medium moves from the end of the inlet 115. Through this, the culture medium flowing in from the outside through the inlet 115 can be smoothly introduced into the internal space (S), and can move evenly to the plurality of supports 123, 223 constituting the support assembly 120, 220, 320 disposed in the internal space (S).

In this invention, the internal surface of the housing in which the outlet 116 is formed may also include a plurality of stepped surfaces 114 like the internal surface of the housing in which the inlet 115 is formed, and the plurality of stepped surfaces 114 may be formed in a form in which the cross-sectional area decreases along the direction in which the culture medium moves. Through this, the culture medium accommodated in the internal space (S) can be smoothly discharged to the outside through the outlet 116 after being gathered toward the outlet 116 through the plurality of stepped surfaces 114.

As a specific example, the housing 110, 210 may include a first box-shaped housing 111, 211 having a first internal space (S1) with an open lower portion and a second box-shaped housing 112, 212 having a second internal spaces (S2) with an open upper portion, as shown in FIGS. 1 to 8.

In this case, the first housing 111, 211 and the second housing 112, 212 may be detachably coupled to each other so that the first internal space (S1) and the second internal space (S2) communicate with each other.

Accordingly, when the first housing 111, 211 and the second housing 112, 212 are coupled to each other, the first internal space (S1) and the second internal space (S2) may be connected to each other to form the internal space (S).

Through this, the housing 110, 210 having the internal space (S) may be manufactured by manufacturing the first housing 111, 211 and the second housing 112, 212 using an upper mold and a lower mold, respectively, and then combining the first housing 111, 211 and the second housing 112, 212, thereby increasing mass productivity.

In this case, the first housing 111, 211 and the second housing 112, 212 may be formed to have different heights, and the inlet 115 and the outlet 116 may be formed in the housing having a relatively larger height among the first housing 111, 211 and the second housing 112, 212, respectively.

As a non-limiting example, the second housing 112, 212 may be formed to have a relatively higher height than that of the first housing 111, 211, and the inlet 115 and the outlet 116 may be formed in the second housing 112, 212.

Accordingly, when the first housing 111, 211 and the second housing 112, 212 are combined, the inlet 115 formed in the second housing 112, 212 may be positioned in the middle of the height of the housing 110, 210. In addition, even if in the housing 110, 210, the internal surface of the portion in which the inlet 115 is formed and/or the portion in which the outlet 116 is formed is formed of a plurality of stepped surfaces 113, 114, the first housing 111, 211 and the second housing 112, 212 can be easily taken out from each mold, so that mass productivity can be maintained.

As another example, as shown in FIGS. 9 to 12, the housing 310 may include a box-shaped body 311 having the internal space (S) with an open upper portion.

In this case, at least one inlet 115 and outlet 116 may be respectively formed on the front and rear surfaces of the body 311, and the internal space (S) with the open upper portion may be sealed with a cover 312 coupled to the housing 310.

The support assembly 120, 220, 320 may be configured in a form in which the plurality of supports 123, 223 is stacked in multiple stages along the height direction. That is, the support assembly 120, 220, 320 may be configured in a modular form in which the plurality of supports 123, 223 is integrated via at least one fastening bar 126.

In this case, the plurality of supports 123, 223 stacked in multiple stages along the height direction may be spaced apart from each other at a predetermined interval.

Through this, in the cell culture apparatus 100, 200, 300 according to an embodiment of the present invention, when the support assembly 120, 220, 320 configured in the form of a module is inserted into the internal space (S) of the housing 110, 210, 310, the plurality of supports 123, 223 may be accommodated in the internal space (S) in a state in which the supports are stacked in multiple stages at an interval from each other.

Accordingly, in the cell culture apparatus 100, 200, 300 according to an embodiment of the present invention, when the support assembly 120, 220, 320 is simply inserted into the internal space (S) of the housing 110, 210, 310, the plurality of supports 123, 223 may be spaced apart from each other at an interval in the internal space (S) of the housing 110, 210, 310 along the height direction of the housing 110, 210, 310.

For this reason, the cell culture apparatus 100, 200, 300 according to an embodiment of the present invention can increase the degree of integration of the supports 123 and 223 disposed in the internal space (S), thereby culturing a large amount of cells through a single culturing process.

In addition, in the cell culture apparatus 110, 200, 300 according to an embodiment of the present invention, the plurality of supports 123, 223 is disposed in a module form in which the plurality of supports 123,223 is arranged in multiple stages in one apparatus, so that a large amount of cell cultures can be conducted, and the overall equipment size can be reduced.

In addition, in the cell culture apparatus 100, 200, 300 according to an embodiment of the present invention, the plurality of supports 123, 223 is configured in a modular form through the support assembly 120, 220, 320, so that the supports can be very easily installed on the internal space (S) of the housing 110, 210, 310 or taken out from the internal space (S).

Figure 2:
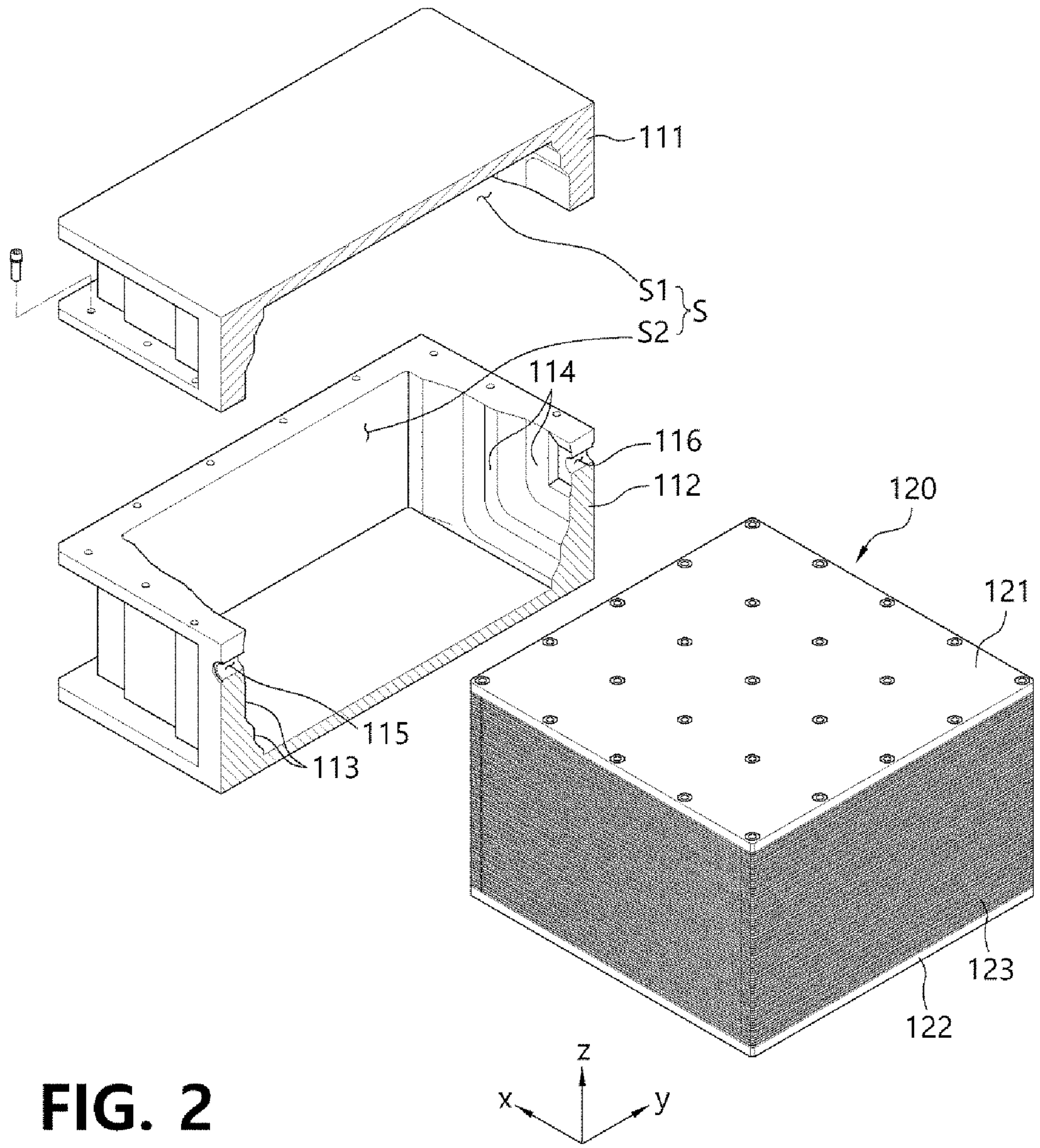
FIG. 2 is a view in which a housing and a support assembly are exploded in a state in which a portion of the housing of FIG. 1 is cut.
Figure 3:
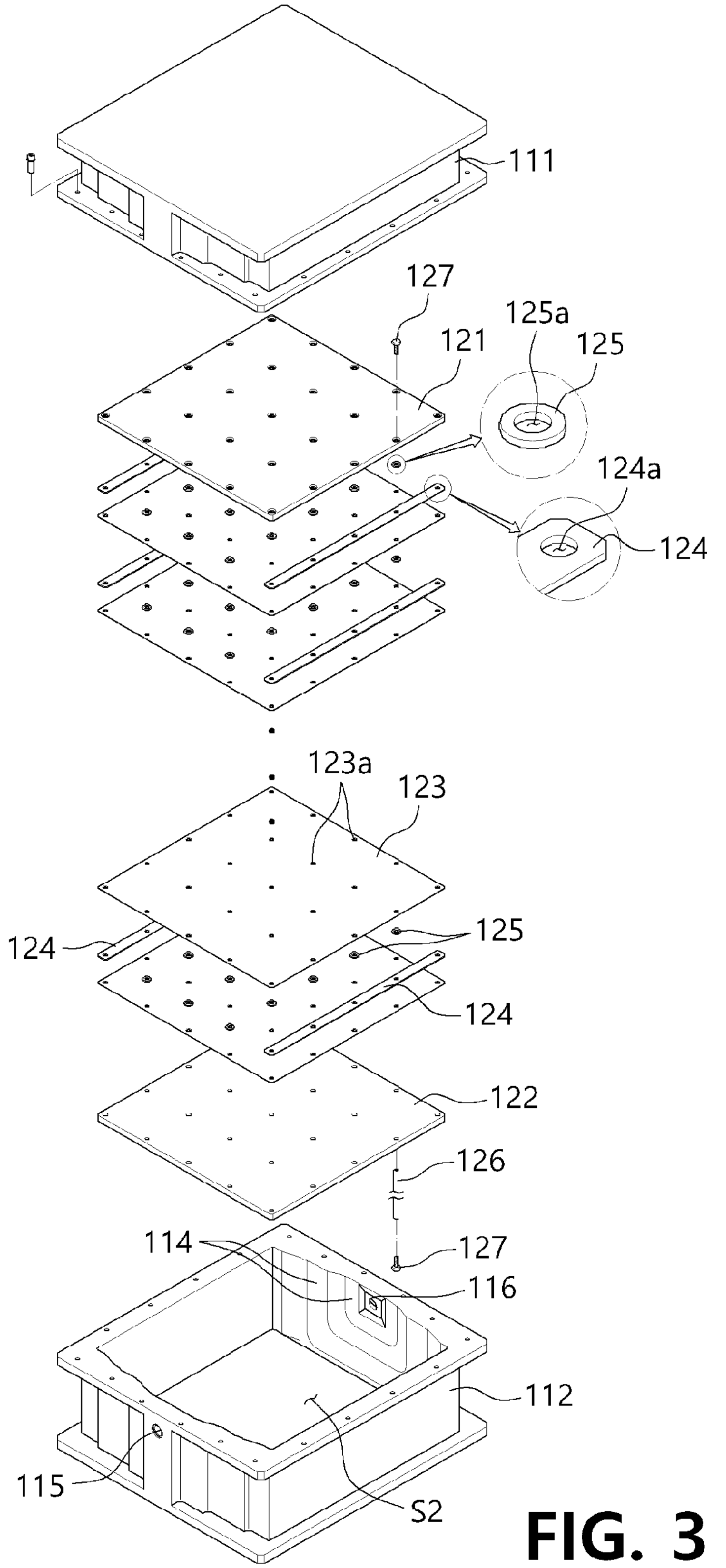
FIG. 3 is an exploded view of 1.
Figure 4:
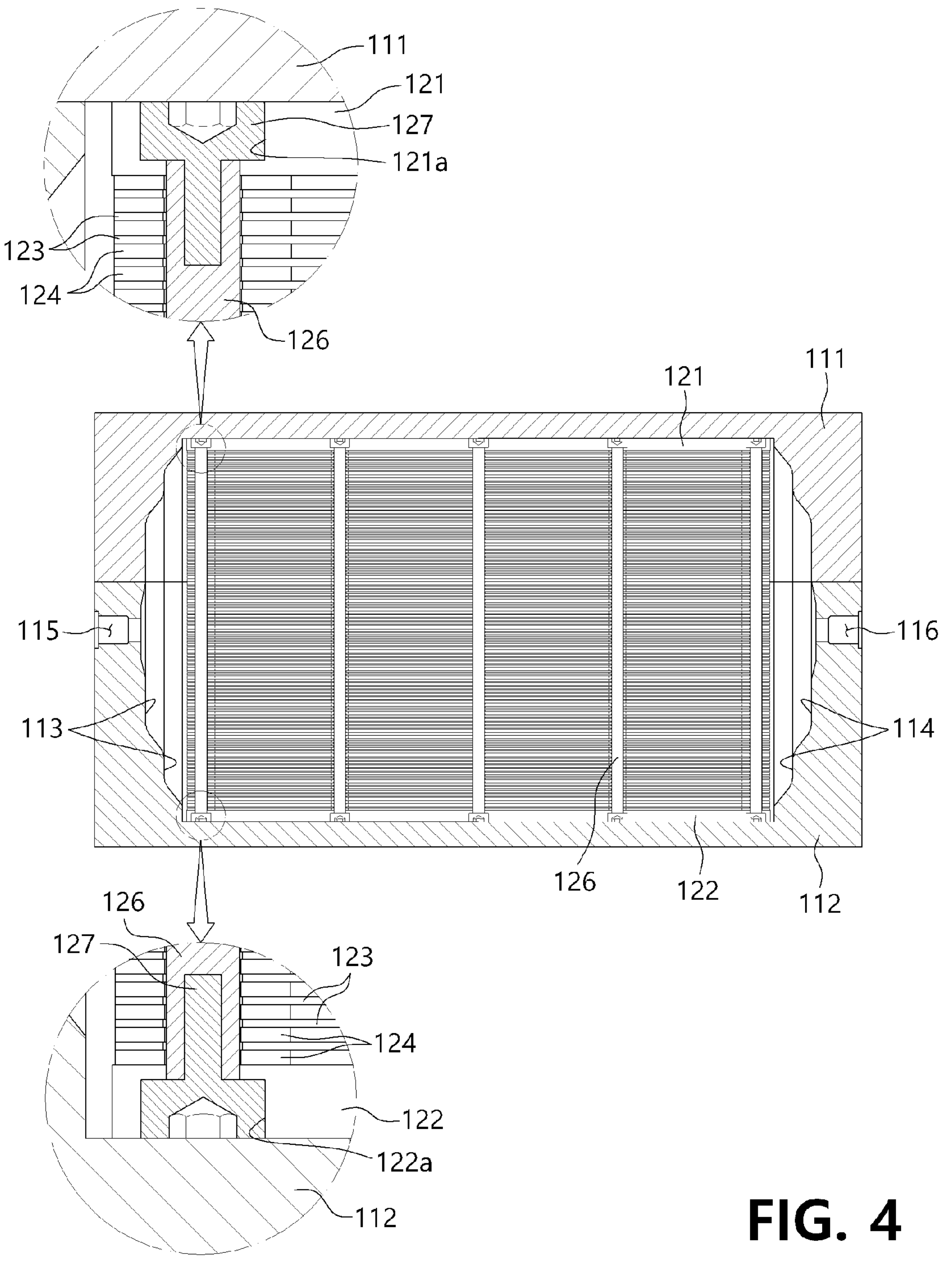
FIG. 4 is a cross-sectional view in the A-A direction of FIG. 1.

To this end, as shown in FIGS. 2 to 4, the support assembly 120 may include the pair of support plates 121, 122 provided in a plate shape having a predetermined area, and the plurality of supports 123 arranged in multiple stages between the pair of support plates 121, 122, and the spacers 124, 125 disposed between the plurality of supports 123 to space the two supports 123 disposed in the up and down directions from each other. The pair of support plates 121, 122, the plurality of supports 123, and the spacers 124, 125 may be fastened to each other through at least one fastening bar 126 having a predetermined length.

Here, the pair of support plates 121, 122, the plurality of supports 123, and the spacers 124, 125 may be fitted to the fastening bar 126, respectively. In this case, the spacers 124, 125 may include a first spacer 124 formed of a plate-shaped member through which a plurality of through holes **124*a* is through-formed so that the plurality of fastening bars 126 having a predetermined length and spaced apart from each other by a predetermined interval can pass therethrough, respectively, a second spacer 125 formed in a ring shape through which a through hole 125*a* is formed so that the fastening bar 126 can pass therethrough. In addition, the support 123 may include a plurality of through holes 123*a* that is through-formed at an interval from each other so that the fastening bar 126** can pass therethrough.

Specifically, the plurality of fastening bars 126 may be spaced apart from each other at a predetermined interval, and the fastening members 127 may be fastened at both ends of the plurality of fastening bars 126. Through this, both ends of the plurality of fastening bars 126 may be fixed to the pair of support plates 121, 122, respectively.

Here, the fastening member 127 may be a bolt member or a nut member. However, the fastening member 127 is not limited to a bolt member or a nut member, and various known members may be used as long as the end of the fastening bar 126 can be fixed to the support plates 121, 122.

In addition, although it has been described that the two fastening members 127 are respectively fastened to both ends of the fastening bar 126, the present invention is not limited thereto, and any one of the two fastening members 127 may be integrally formed to one end of the fastening bar 126. For example, the fastening bar 126 may be configured in a form in which a bolt head is formed on one end.

In this case, the support 123 and the spacers 124, 125 may be fastened to the fastening bar 126 through the through holes 123*a*, 124*a*, 125*a*.

In this case, the plurality of spacers 124, 125 and the plurality of supports 123 may be alternately fastened to the respective fastening bar 126, and the plurality of supports 123 and the spacers 124, 125 may be disposed to be positioned between the pair of support plates 121, 122.

Accordingly, the spacers 124, 125 may be respectively disposed between the two supports 123 disposed vertically along the height direction. Through this, the plurality of supports 123 can maintain a plate shape through the plurality of fastening bars 126, and the two supports 123 disposed in the up and down directions may maintain a state spaced apart by a predetermined interval through the spacers 124, 125.

For this reason, both sides of the plurality of supports 123 disposed in the up and down directions can be in smooth contact with the culture medium filled in the internal space (S).

Here, the plurality of fastening bars 126 may be spaced apart to be positioned in the edge region and internal region of the support 123, and the pair of first spacers 124 may be disposed to be positioned at both ends along the width direction of the support 123, and the second spacer 125 may be disposed to be positioned in the internal region of the support 123.

That is, the pair of first spacers 124 is fastened to the plurality of fastening bars 126 disposed in the longitudinal direction in the edge region of the support 123, and thus, may be disposed to be positioned on the both ends along the width direction of the support 123. The second spacer 125 is individually fastened to the respective fastening bar 126 positioned in the internal region of the support 123, and thus, may be disposed to be positioned in the internal region of the support 123.

Through this, the culture medium introduced into the internal space (S) through the inlet 115 can be blocked from moving toward both ends of the support 123 through the pair of first spacers 124.

For this reason, the cell culture apparatus 100 according to an embodiment of the present invention can minimize the use of unnecessary culture medium while reducing the amount of culture medium filled in the internal space (S).

In this case, the support assembly 120 may be configured so that the fastening members 127 fastened to both end of the fastening bar 126 do not protrude outward from one surface of the support plates 121, 122.

For example, as shown in FIG. 4, the pair of support plates 121, 122 may include receiving grooves 121*a*, 122*a* that are drawn in from one surface to accommodate the fastening members 127 fastened to both ends of the fastening bar 126, respectively.

Accordingly, in the support assembly 120, one surface of the pair of support plates 121, 122 may be in close contact with the internal surface of the housing 110. Through this, the cell culture apparatus 100 according to an embodiment of the present invention can minimize the inflow of the culture medium introduced into the internal space (S) through the inlet 115 into the space between the support plates 121, 122 on which the support 123 is not disposed and the internal surface of the housing 110, and the culture medium introduced into the internal space (S) through the inlet 115 can only fill the space between the pair of support plates 121, 122.

For this reason, the cell culture apparatus 100 according to an embodiment of the present invention can minimize the use of unnecessary culture medium while reducing the amount of culture medium filled in the internal space (S).

In addition, since the fastening member 127 does not protrude outward from one surface of the support plates 121, 122, a separate receiving groove for accommodating the fastening member 127 may be unnecessary in the internal surface of the housing 110.

Accordingly, compared with the case where the receiving groove for accommodating the fastening member 127 is formed in the internal surface of the housing 110, the cell culture apparatus 100 according to this embodiment can fundamentally solve the problem of the culture medium accumulating in the receiving groove.

In particular, when the cell culture apparatus 100 according to an embodiment of the present invention is applied to a circulation type cell culture system in which the culture medium is circulated, it is possible to solve the problem of stagnation due to the accumulation of culture medium in the receiving groove.

As another example, as shown in FIGS. 6 to 8, 10 to 12, the support assembly 220 may include the pair of support plates 121, 122 provided in a plate shape having a predetermined area, the plurality of supports 223 arranged in multiple stages between the pair of support plates 121, 122, the spacer 125 disposed between the plurality of supports 223 to space the two supports 223 disposed in the up and down directions from each other. The pair of support plates 121, 122, the plurality of supports 223, and the spacer 125 may be fastened to each other through at least one fastening bar 126 having a predetermined length.

Here, the pair of support plates 121, 122, the plurality of supports 223, and the spacer 125 may be fitted to the fastening bar 126, respectively. In this case, the spacer 125 may be composed of only the second spacer 125 formed in a ring shape through which the through hole 125*a* is formed so that the fastening bar 126 can pass therethrough, and the support 223 may include the plurality of through holes 223*a* which is through-formed at an interval from each other so that the fastening bar 126 can pass therethrough.

Figure 6:
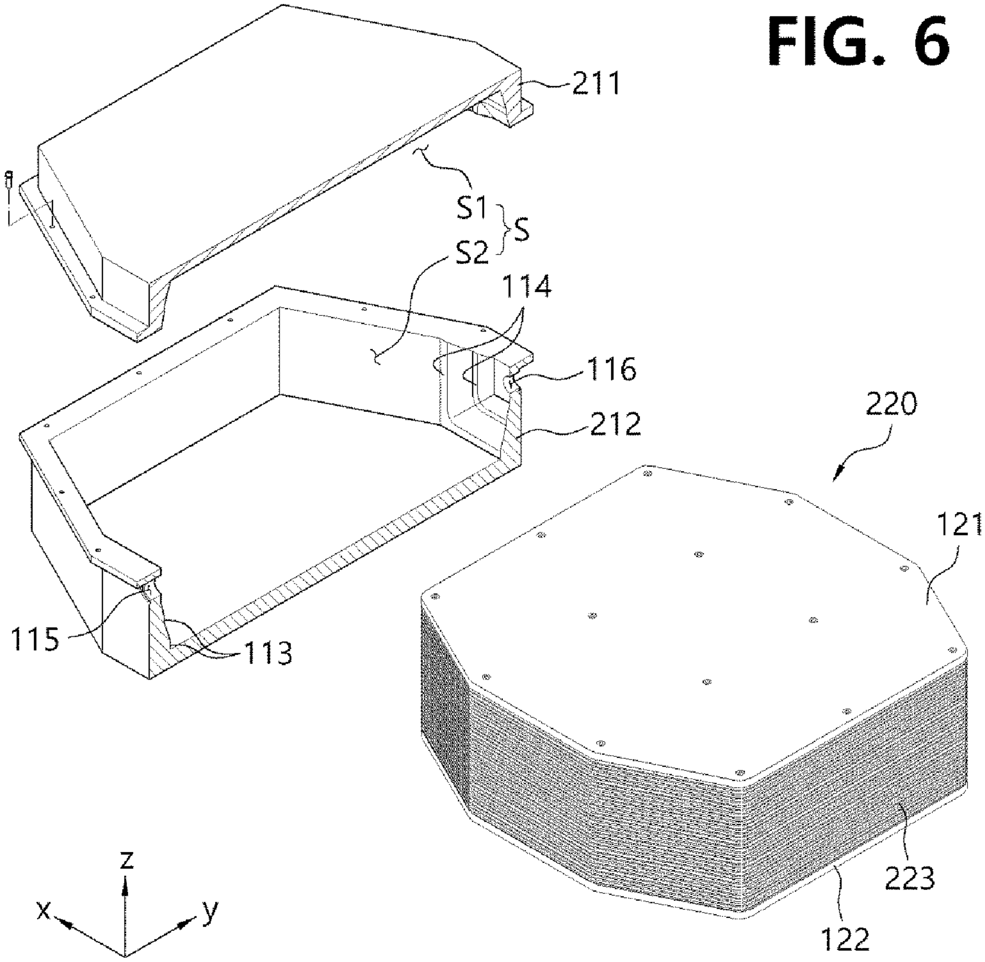
FIG. 6 is a view in which a housing and a support assembly are exploded in a state in which a portion of the housing of FIG. 5 is cut.
Figure 7:
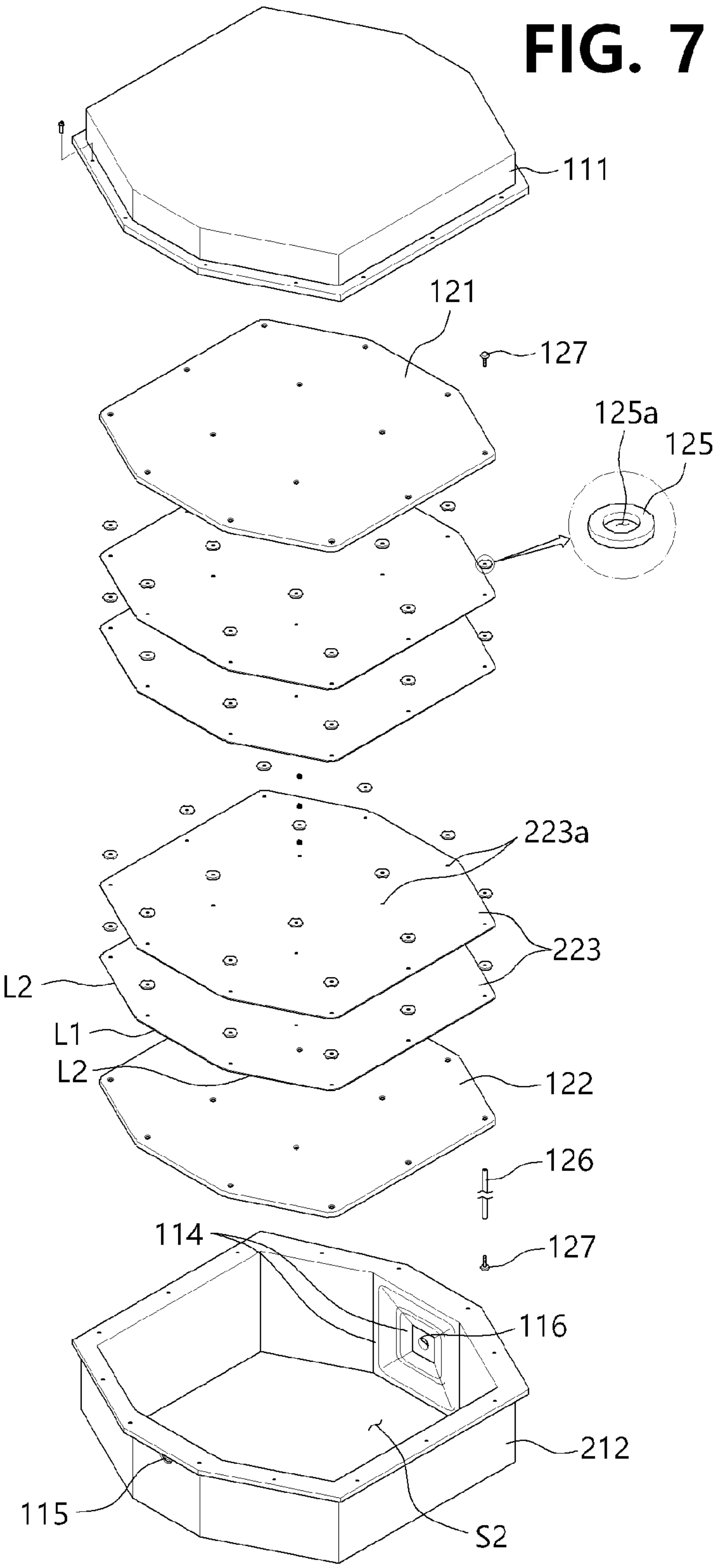
FIG. 7 is an exploded view of FIG. 5.

Specifically, as shown in FIGS. 2 and 6, the plurality of fastening bars 126 may be spaced apart from each other at a predetermined interval, and the fastening members 127 may be fastened to both ends of the plurality of fastening bars 126. Through this, the plurality of fastening bars 126 may be fixed with the pair of supports 121, 122 at both ends, respectively.

Here, the fastening member 127 may be a bolt member or a nut member. However, the fastening member 127 is not limited to a bolt member or a nut member, and various known members may be used as long as the end of the fastening bar 126 can be fixed to the support plates 121, 122. In addition, although it has been described that the two fastening members 127 are respectively fastened to both ends of the fastening bar 126, the present invention is not limited thereto, and any one of the two fastening members 127 may be integrally formed on the end of the fastening bar 126. For example, the fastening bar 126 may be configured in a form in which a bolt head is formed on one end.

In this case, the support 223 and the spacer 125 may be fastened to the fastening bar 126 through the through holes 223*a*, 125*a*.

In this case, the plurality of second spacers 125 and the plurality of supports 223 may be alternately fastened to the respective fastening bar 126, and the plurality of supports 223 and the spacers 125 may be disposed to be positioned between the pair of support plates 121, 122.

Accordingly, the second spacer 125 may be respectively disposed between the two supports 223 disposed vertically in the height direction. Through this, the plurality of supports 223 can maintain a plate shape through the plurality of fastening bars 126, and the two supports 223 disposed in the up and down directions may maintain a state spaced apart from each other by a predetermined distance through the second spacer 125.

For this reason, both sides of the plurality of supports 223 disposed in the up and down directions can be in smooth contact with the culture medium filled in the internal space (S).

In this case, the support assembly 220 may be configured such that the fastening members 127 fastened to both ends of the fastening bar 126 do not protrude outward from one surface of the support plates 121, 122.

Figure 8:
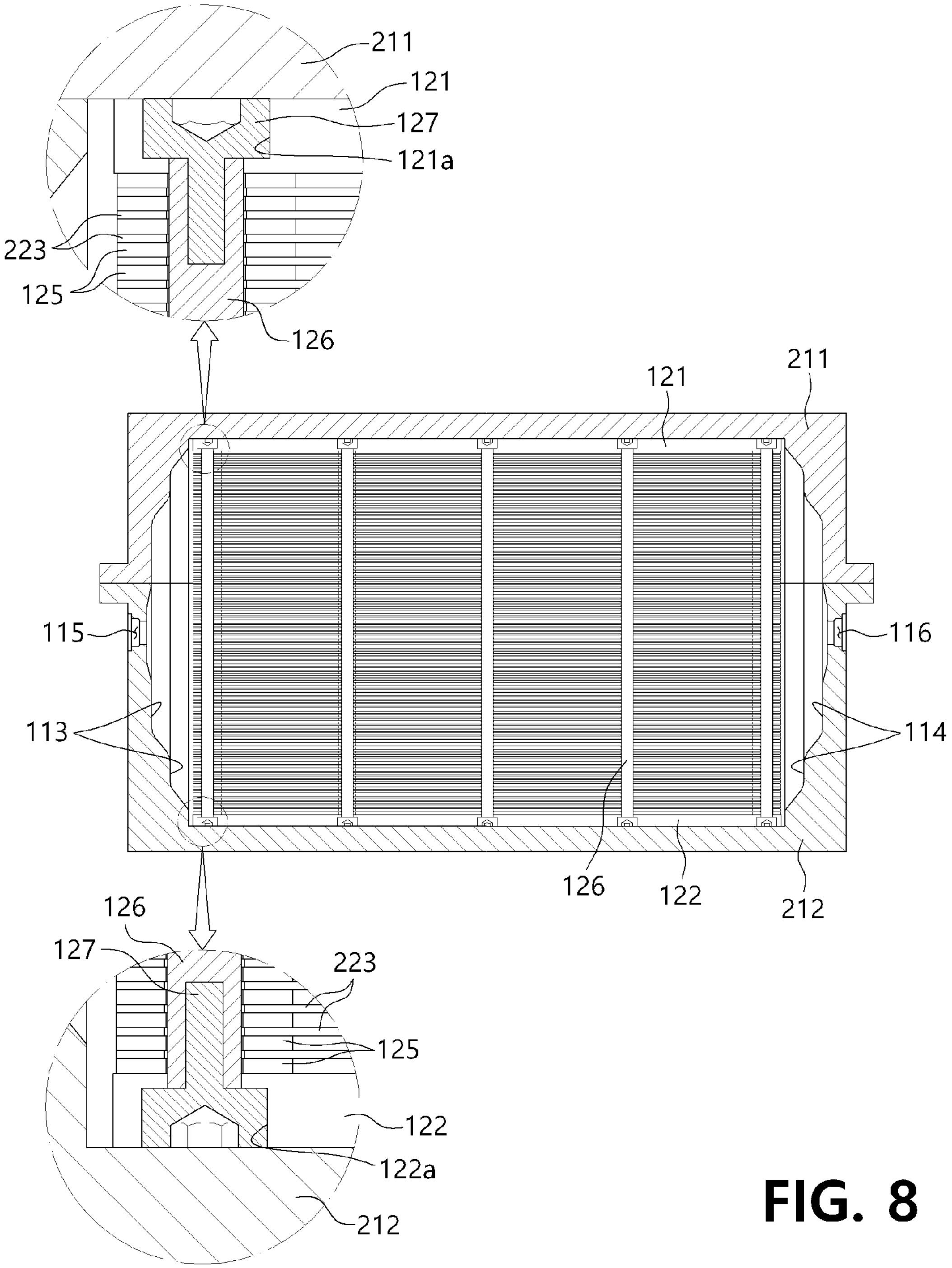
FIG. 8 is a cross-sectional view in the B-B direction of FIG. 5.
Figure 12:
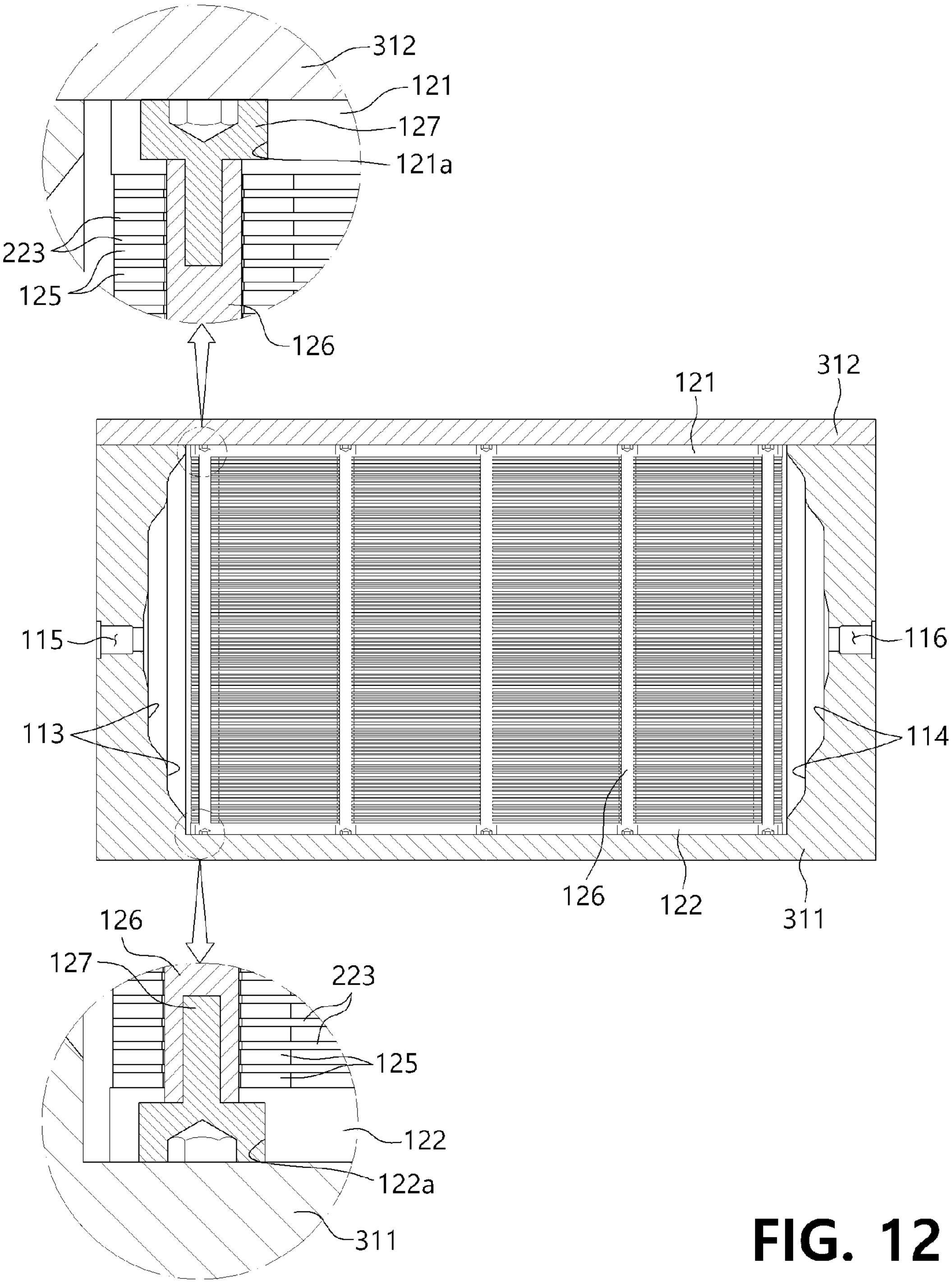
FIG. 12 is a cross-sectional view in the C-C direction of FIG. 9.

For an example, as shown in FIGS. 8 and 12, the pair of support plates 121, 122 may include the receiving grooves 121*a*, 122*a* that are drawn in from one surface to accommodate the fastening members 127 respectively fastened to both ends of the fastening bar 126.

Accordingly, in the support assembly 220, one surface of the pair of support plates 121, 122 may be in close contact with the internal surface of the housing 210, 310. Through this, the cell culture apparatus 200, 300 according to an embodiment of the present invention can minimize the inflow of the culture medium introduced into the internal space (S) through the inlet 115 to the space between the support plates 121, 122 on which the support 223 is not disposed and the internal surface of the housing 210, 310, and the culture medium introduced into the internal space (S) through the inlet 115 can only fill the space between the pair of support plates 121, 122.

For this reason, the cell culture apparatus 200, 300 according to an embodiment of the present invention can minimize the use of unnecessary culture medium while reducing the amount of culture medium filled in the internal space (S).

In addition, since the fastening member 127 does not protrude outward from one surface of the support plates 121, 122, a separate accommodation groove for accommodating the fastening member 127 may be unnecessary in the internal surface of the housing 210, 310.

Accordingly, compared with the case where the receiving groove for accommodating the fastening member 127 is formed in the internal surface of the housing 210, 310, the cell culture apparatus 200, 300 according to this embodiment can fundamentally solve the problem of the culture medium accumulating in the receiving groove.

In particular, when the cell culture apparatus 200, 300 according to an embodiment of the present invention is applied to a circulation type cell culture system in which the culture medium is circulated, the problem of stagnation due to the accumulation of culture medium in the receiving groove.

Figure 13:
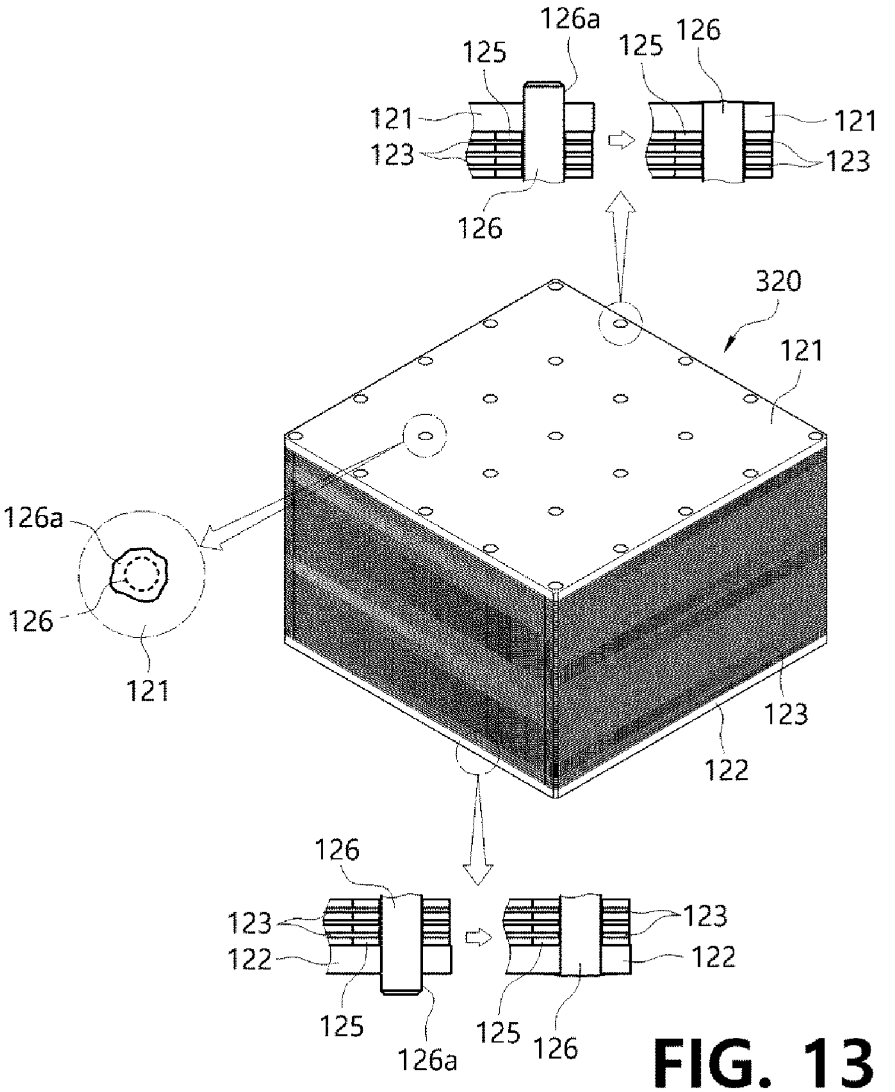
FIG. 13 is a view showing another type of a support assembly that can be applied to a cell culture apparatus according to the present invention.
Figure 14:
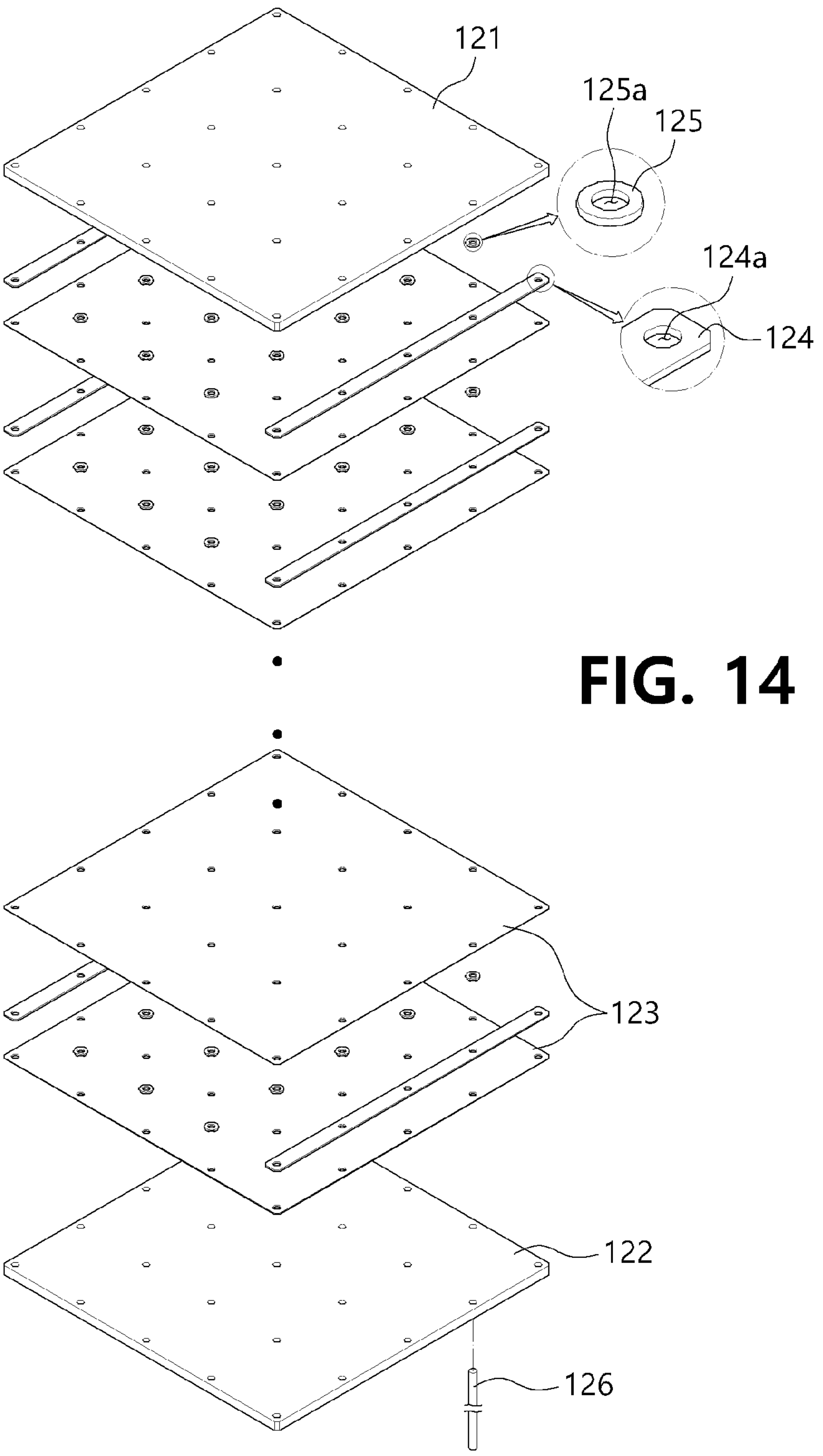
FIG. 14 is an exploded view in a state before the protrusion is melted through thermal fusion in FIG. 13.

As another example, as shown in FIGS. 13 and 14, the support assembly 320 may include the pair of support plates 121, 122 provided in a plate shape having a predetermined area, the plurality of supports 123 arranged in multiple stages between the pair of support plates 121, 122, and the spacers 124, 125 that are disposed between the plurality of supports 123 and space the two supports 123 disposed in the up and down directions from each other. In addition, the pair of support plates 121, 122, the plurality of supports 123, and the spacers 124, 125 may be fastened to each other through at least one fastening bar 126 having a predetermined length.

Here, the pair of support plates 121, 122, the plurality of supports 123, and the spacers 124, 125 may be fitted to the fastening bar 126, respectively. In this case, the spacers 124, 125 may include the first spacer 124 formed of a plate-shaped member through which the plurality of through holes 124*a* is formed so that the plurality of fastening bars 126 having a predetermined length and spaced apart from each other by a predetermined interval can pass therethrough, and the second spacer 125 formed in a ring shape through which a through hole 125*a* is formed so that the fastening bar 126 can pass therethrough. In addition, the support 123 may include the plurality of through holes 123*a* that is through-formed at an interval from each other so that the fastening bar 126 can pass therethrough.

Specifically, as shown in FIG. 13, the plurality of fastening bars 126 may be spaced apart from each other at a predetermined interval, and the plurality of fastening bars 126 may have a protruding portion 126*a* whose both ends pass through a pair of support plates 121, 122 and protrude outward by a predetermined length.

As can be seen from the enlarged view of FIG. 13, such a protruding portion 126*a* is melted through thermal fusion in a state protruded by a predetermined length to the outside of the support plates 121, 122 and fixed to one surface of the support plates 121, 122. Through this, both ends of the plurality of fastening bars 126 may be respectively fixed to the pair of support plates 121, 122 through the protruding portion 126*a*.

In this case, the support 123 and the spacers 124, 125 may be respectively fastened to the fastening bar 126 through the through holes 123*a*, 124*a*, 125*a*.

In this case, the plurality of spacers 124, 125 and the plurality of supports 123 may be alternately fastened to the respective fastening bar 126, and the plurality of supports 123 and the spacers 124, 125 may be disposed to be positioned between the pair of supports 121, 122.

Accordingly, the spacers 124, 125 may be respectively disposed between the two supports 123 disposed vertically in the height direction. Through this, the plurality of supports 123 can maintain a plate shape through the plurality of fastening bars 126, and the two supports 123 arranged in the up and down directions may maintain a state spaced by a predetermined interval through the spacers 124, 125.

For this reason, both sides of the plurality of supports 123 arranged in the up and down directions can be in smooth contact with the culture medium filled in the internal space (S).

Here, the plurality of fastening bars 126 may be spaced apart from each other so as to be disposed in the edge region and internal region of the support 123, and the pair of first spacers 124 may be disposed to be positioned at both ends along the width direction of the support 123, and the second spacer 125 may be disposed to be positioned in the internal region of the support 123.

That is, the pair of first spacers 124 is fastened to the plurality of fastening bars 126 disposed in the longitudinal direction in the edge region of the support 123, and may be disposed to be positioned at both sides along the width direction of the support 123. The second spacer 125 is individually fastened to the respective fastening bar 126 positioned in the internal region of the support 123 to be positioned in the internal region of the support 123.

Through this, the culture medium introduced into the internal space (S) through the inlet 115 can be blocked from moving toward both ends of the support 123 through the pair of first spacers 124.

For this reason, the cell culture apparatus to which the support assembly 320 according to the present embodiment is applied can minimize the use of unnecessary culture medium while reducing the amount of the culture medium filled in the internal space (S).

In addition, in the support assembly 320 according to the present embodiment, the protruding portions **126*a* formed on both ends of the fastening bar 126 are melted through thermal fusion and fixed to one surface of the supports 121, 122, so that the protruding portion 126*a* may not protrude outward from one surface of the support plates 121, 122**.

Accordingly, in the support assembly 320, one surface of the pair of support plates 121, 122 may be in close contact with the internal surface of the housing. Due to this, the culture medium introduced into the internal space (S) through the inlet 115 can be minimized from flowing into the space between the support plates 121, 122 where the support 123 is not disposed and the internal surface of the housing, and the culture medium introduced into the internal space (S) through the inlet 115 can fill only the space between the pair of support plates 121, 122.

For this reason, the cell culture apparatus to which the support assembly 320 according to the present embodiment is applied can minimize the use of unnecessary culture medium while reducing the amount of culture medium filled in the internal space (S). In addition, since the protruding portion **126*a* does not protrude outwardly from one surface of the support plates 121, 122, a separate receiving groove for accommodating the protruding portion 126*a* in the internal surface of the housing may be unnecessary. Accordingly, compared with the case where the receiving groove for accommodating the protruding portion 126*a*** is formed in the internal surface of the housing, the problem of the culture medium accumulating in the receiving groove can be fundamentally prevented.

The support assembly 320 according to the present embodiment may replace the support assembly 120, 220 shown in FIGS. 1 to 12, and the support 123 constituting the support assembly 320 may employ the support 223 shown in FIGS. 5 to 12.

Meanwhile, the cell culture apparatus 200, 300 according to an embodiment of the present invention may be configured to smoothly supply the culture medium introduced through one inlet 115 to the support 223 having a large area, even if the support 223 is implemented with a large area.

That is, even if the support 223 is implemented with a large area, the dead space of the internal space (S) in which the support assembly 220, 320 including the support 223 is accommodated is reduced, and thus, the culture medium introduced through one inlet 115 may be smoothly supplied to the support 223 having a large area.

To this end, as shown in FIGS. 5 to 12, the support 223 may be formed in a polygonal shape including a straight side (L1) and a pair of inclined sides (L2) extending in a direction away from each other while being inclined at a predetermined angle from both ends of the straight side (L1).

As an example, the support 223 may be formed in an approximately octagonal shape.

In this case, the internal space (S) of the housing 210, 310 may also be formed to have substantially the same cross-sectional shape as the support 223.

In this case, the inlet 115 and outlet 116 formed in the housing 210, 310 may be formed to be positioned at position corresponding to the straight side (L1) of the support 223 in order to supply the culture medium to the internal space (S).

Accordingly, the culture medium introduced through the inlet 115 flows into the straight side (L1) of the support 223 and then smoothly moves to the left and right sides along the inclined side (L2) of the support 223, and then, can move backwards along the longitudinal direction of the support 223.

For this reason, in the cell culture apparatus 200 and 300 according to the present embodiment, the culture medium introduced through one inlet 115 can be smoothly supplied to the support having a large area even if the support 223 is implemented with a large area and one inlet 115 for introducing the culture medium into the internal space (S) is provided in the housing 210, 310. Also, a large amount of cells attached to the support 223 implemented in a large area can be smoothly cultured.

Meanwhile, cells to be cultured may be attached to the plurality of supports 123, 223 constituting the support assembly 120, 220, 320, and the cells attached to the supports 123, 223 may be supplied with nutrients from the culture medium filled in the internal space (S). Through this, the cells attached to the plurality of supports 123, 223 can be cultured through nutrients supplied from the culture medium.

These supports 123, 223 may be provided in a plate shape having a predetermined area so that a large amount of cells can be cultured through one culture process.

Here, as long as the supports 123, 223 can be implemented in a plate shape and easily attach cells, various known materials used in cell culture can be used without limitation.

Figure 15:
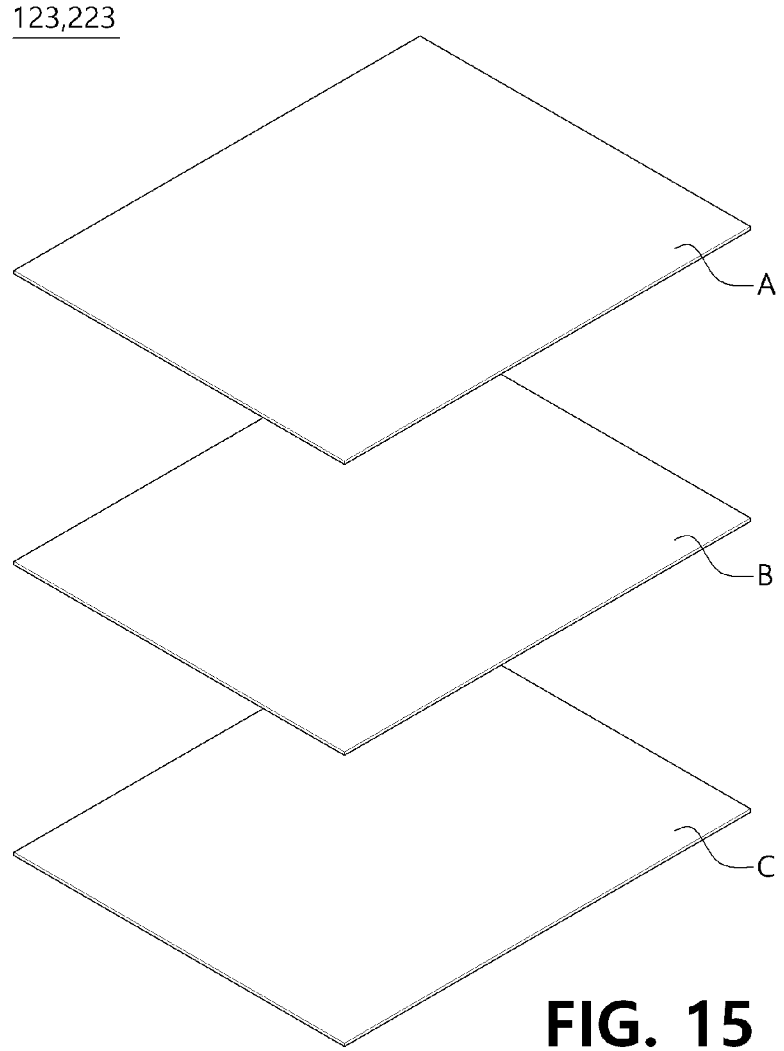
FIG. 15 is a view showing a type of a support that can be applied to a cell culture apparatus according to the present invention.

As a non-limiting example, the support 123, 223 may include a nanofiber membrane (A) in which the nanofibers are formed into a three-dimensional network structure through electrospinning. In this case, the support 123, 223, as shown in FIG. 15, may have a three-layer structure that further includes a support member (C) attached to one surface of the nanofiber membrane (A) through an adhesive layer (B) in addition to the nanofiber membrane (A).

In this case, the support member (C) may be a plate-shaped film member. Through this, even if the nanofiber membrane (A) is formed in a flexible plate shape, it can be supported through the support member (C), thereby preventing bending or sagging. Accordingly, the support 123, 223 disposed in the internal space (S) of the housing 110, 210, 310 can maintain an unfolded state, so that cells can be smoothly cultured.

Figure 16:
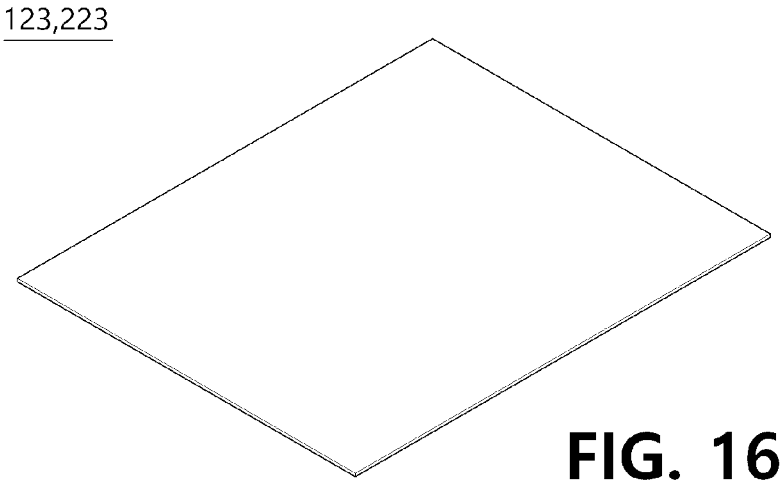
FIG. 16 is a view showing another type of a support that can be applied to a cell culture apparatus according to the present invention.

As another example, the support 123, 223 may be formed of a plate-shaped film member having a predetermined area as shown in FIG. 16.

In this case, the support 123, 223 may have a modified surface so that cells to be cultured can be smoothly attached. For example, when the support 123, 223 is the nanofiber membrane (A), the nanofiber membrane (A) may be a membrane in which the surface of the nanofibers is coated with a protein motif. In addition, when the support 123, 223 is provided with a plate-shaped film member, the film member may be a plasma-treated film member.

Accordingly, the cells to be cultured can be smoothly attached to the surface of the support 123, 223, and the cells to be cultured can be cultured through nutrients supplied from the culture medium in a state attached to the surface of the support 123, 223.

However, the type of the support 123, 223 is not limited thereto, and various materials used for cell culture known in the art may be used as long as they can be implemented in a plate shape and easily attach cells.

The cell culture apparatus 100, 200, 300 according to an embodiment of the present invention described above may be applied to a circulating type cell culture system in which the culture medium supplying nutrients to the cells circulates through a culture medium supply unit (not shown) and the cell culture apparatus 100, 200, 300, and it may be also applied to a non-circulation type cell culture system in which the culture medium is not replaced until the cell culture is completed in a state in which the culture medium is filled in the internal space (S) of the cell culture apparatus 100, 200, 300.

An embodiment of the present invention has been described above, but the spirit of the present invention is not limited to the embodiments presented in this specification, and those skilled in the art who understand the spirit of the present invention will be able to easily suggest other embodiments by addition, change, deletion, addition, etc. of components within the scope of the same idea, but this will be also within the scope of the present invention.

The invention claimed is:

1. A cell culture apparatus, comprising:

a housing including an internal space filled with a culture medium for cell culture; and a support assembly including a pair of support plates provided in a plate shape having a predetermined area, a plurality of supports disposed in multiple stages between the pair of support plates, a spacer disposed between the plurality of supports to space the supports apart from each other at a predetermined interval along one direction, a plurality of fastening bars for mutually fastening the pair of support plates, the plurality of supports, and the spacer, and a fastening member fastened to an end of at least one of the plurality of fastening bars, wherein the support assembly is inserted in the internal space in a state where the plurality of supports is coupled to each other via the plurality of fastening bars, wherein the support assembly is configured in a modular form in which the plurality of supports is integrated via the plurality of fastening bars so that the support assembly is configured to be integrally installed in the internal space or integrally taken out from the internal space, wherein each support plate of the pair of support plates includes a receiving groove formed to be recessed inward from an outer surface of the support plate to a predetermined depth, wherein the fastening member is accommodated in the receiving groove and does not protrude outwardly from the outer surface of the support plate, such that the outer surface of the support plate is in close contact with an internal surface of the housing when the support assembly is integrally installed in the internal space.

2. The cell culture apparatus according to claim 1, wherein the housing includes a first housing having a first internal space with an open lower portion, and a second housing detachably coupled to the first housing and having a second internal space with an open upper portion, and the internal space is formed by connecting the first internal space and the second internal space to each other when the first and second housings are combined.

3. The cell culture apparatus according to claim 2, wherein the first housing and the second housing have different heights, and an inlet for supplying the culture medium to the internal space is formed in the housing having a larger height among the first housing and the second housing.

4. The cell culture apparatus according to claim 1, wherein the housing includes an inlet for supplying the culture medium to the internal space, and the internal surface of the housing in which the inlet is formed of a plurality of stepped surfaces whose cross-sectional area increases from the inlet toward an edge.

5. The cell culture apparatus according to claim 1, wherein the plurality of supports has a polygonal shape having a first side and a pair of inclined sides extending in a direction away from each other while being inclined at a predetermined angle from both ends of the first side, and an inlet for supplying the culture medium to the internal space is formed in the housing to be positioned at a position corresponding to the first side.

6. The cell culture apparatus according to claim 5, wherein the housing includes a first housing having a first internal space with an open lower portion, and a second housing detachably coupled to the first housing and having a second internal space with an open upper portion, the second housing has a height different from that of the first housing, and the inlet for supplying the culture medium to the internal space is formed in the housing having a larger height among the first housing and the second housing.

7. The cell culture apparatus according to claim 5, wherein the housing includes a body having the internal space with an open upper portion, and a cover fastened to the body to cover the open upper portion of the internal space.

8. The cell culture apparatus according to claim 1, wherein each of the plurality of supports includes a plate-shaped nanofiber membrane coated with a protein motif, and a support member attached to one surface of the nanofiber membrane via an adhesive layer to support the nanofiber membrane.

9. The cell culture apparatus according to claim 1, wherein each of the plurality of supports is a plasma-treated plate-shaped film member.

10. The cell culture apparatus according to claim 1, wherein the spacer includes a pair of first spacers having a predetermined length and a plate shape, and the pair of first spacers is disposed to be positioned at both ends along a width direction of the plurality of supports.

11. The cell culture apparatus according to claim 10, wherein the spacer further includes at least one second spacer formed in a ring shape, and the second spacer is disposed to be positioned in an internal region of the plurality of supports.

* * * * *